United States Patent [19]
Chanoch

[11] Patent Number: 5,645,534
[45] Date of Patent: Jul. 8, 1997

[54] TIME OF LAST INJECTION INDICATOR FOR MEDICATION DELIVERY PEN

[75] Inventor: Lawrence H. Chanoch, Mahwah, N.J.

[73] Assignee: Becton Dickinson and Company, Franklin Lakes, N.J.

[21] Appl. No.: 267,097

[22] Filed: Jun. 24, 1994

[51] Int. Cl.6 .................. A61M 3/00; A61M 5/00
[52] U.S. Cl. ............ 604/189; 604/187; 604/211; 206/534
[58] Field of Search ................ 604/110, 192, 604/111, 194–198, 263, 208–211, 218, 187, 189, 232; 128/919; 206/364–366, 459.1, 534, 537; 433/89, 90

[56] References Cited

U.S. PATENT DOCUMENTS

|  |  |  |  |
|---|---|---|---|
| 140,842 | 7/1873 | Rembert | 206/459.1 X |
| 2,706,464 | 4/1955 | North | 206/534 X |
| 2,884,123 | 4/1959 | Dann et al. | 206/365 |
| 3,232,117 | .2/1966 | Gilmont | 604/211 X |
| 3,766,882 | 10/1973 | Babbitt, III | 206/459.1 X |
| 3,815,785 | 6/1974 | Gilmont | 604/211 X |
| 3,960,713 | 6/1976 | Carey | 206/459.1 X |
| 3,996,879 | 12/1976 | Walton | 206/534 X |
| 4,049,408 | 9/1977 | Ford | 206/534 |
| 4,466,426 | 8/1984 | Blackmun | 604/210 X |
| 4,505,702 | 3/1985 | Peery et al. | 604/209 |
| 5,104,380 | 4/1992 | Holman et al. | 604/117 |
| 5,308,340 | 5/1994 | Harris | 604/208 |
| 5,320,609 | 6/1994 | Haber et al. | 604/135 |
| 5,358,117 | 10/1994 | Adams | 206/534 |
| 5,366,113 | 11/1994 | Kim et al. | 221/232 |
| 5,433,324 | 7/1995 | Leonard | 206/534 |
| 5,482,163 | 1/1996 | Hoffman | 206/534 |
| 5,489,275 | 2/1996 | Thompson et al. | 604/264 |

*Primary Examiner*—Michael Powell Buiz
*Assistant Examiner*—V. Alexander
*Attorney, Agent, or Firm*—Alan W. Fiedler

[57] ABSTRACT

A medication delivery pen is provided with an indicator that displays the time of last injection through interaction between a cap and pen body assembly. When a user requires an injection the cap is removed from the pen and a dose is set by turning a dose setting knob to the desired dose as displayed in a window in the pen. After the desired dose is set using the dose setting knob, injection is achieved by pushing an actuator button. After injection the user replaces the cap on the pen such that indicia on the cap align with indicia on the body of the pen to display the day and time of day of the last injection, thereby providing the user with means for remembering when the last injection was administered by aligning indicia on the cap with indicia on the pen body assembly, without having to otherwise write or record the day and time of the last injection.

7 Claims, 5 Drawing Sheets

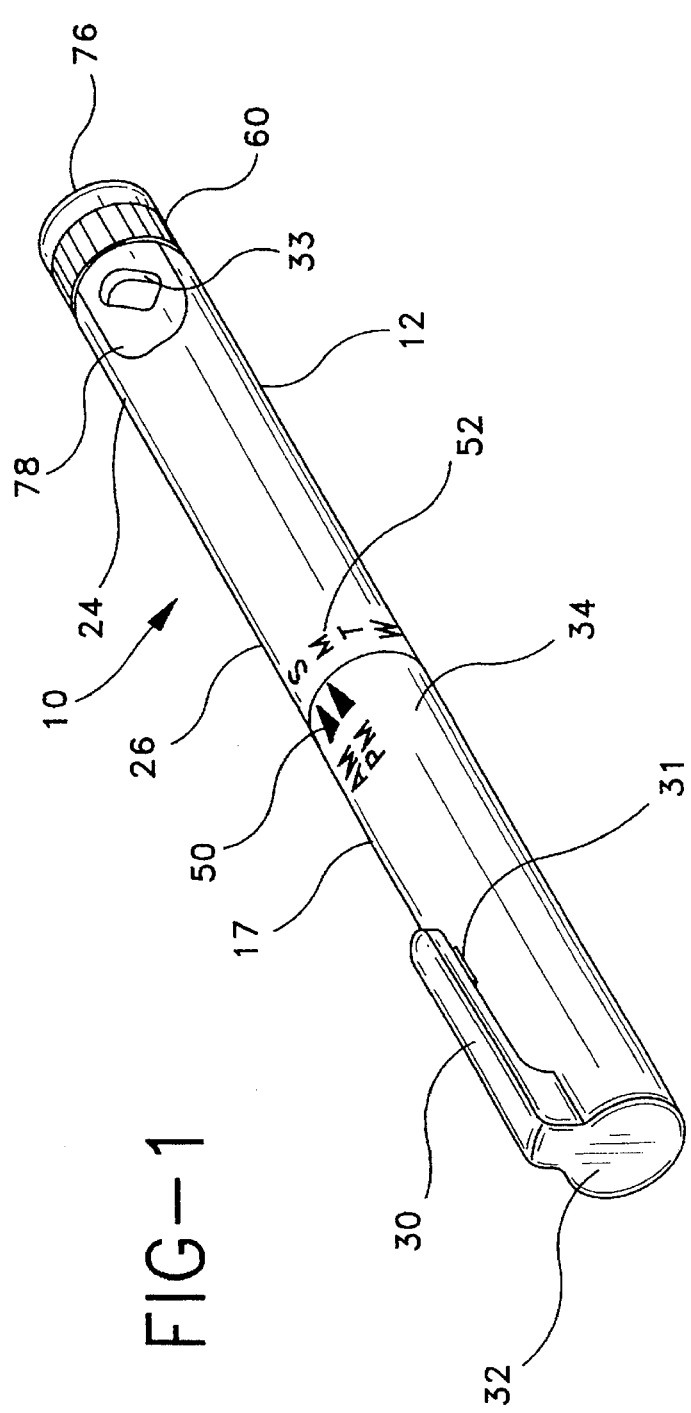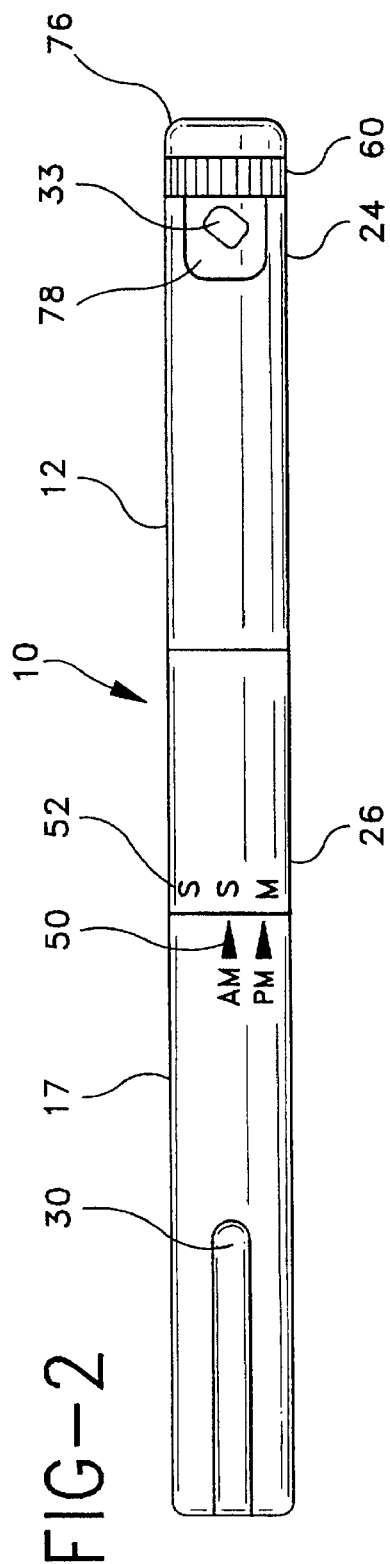

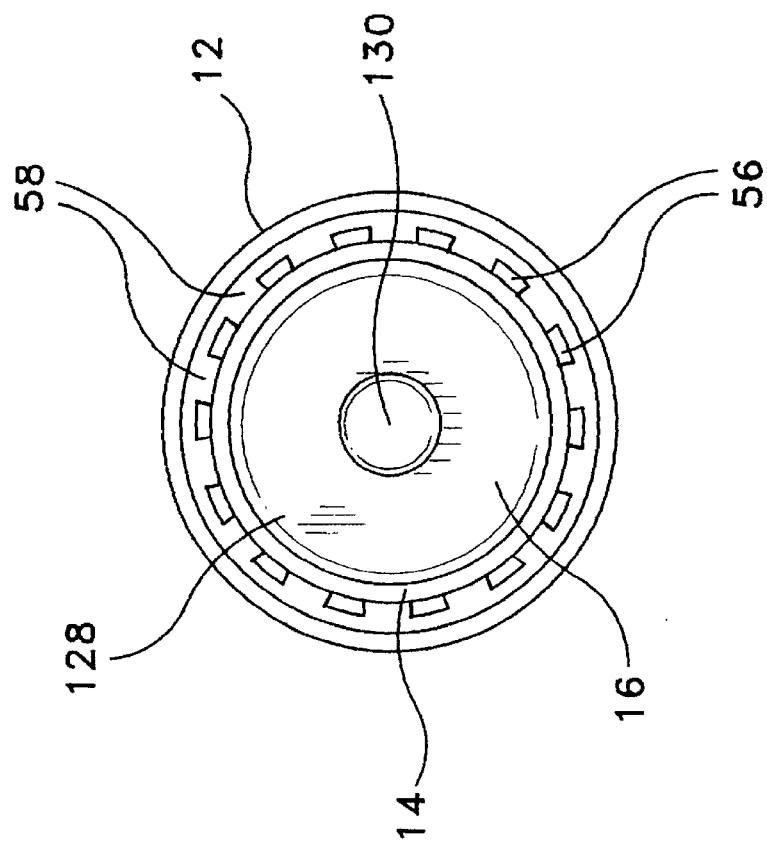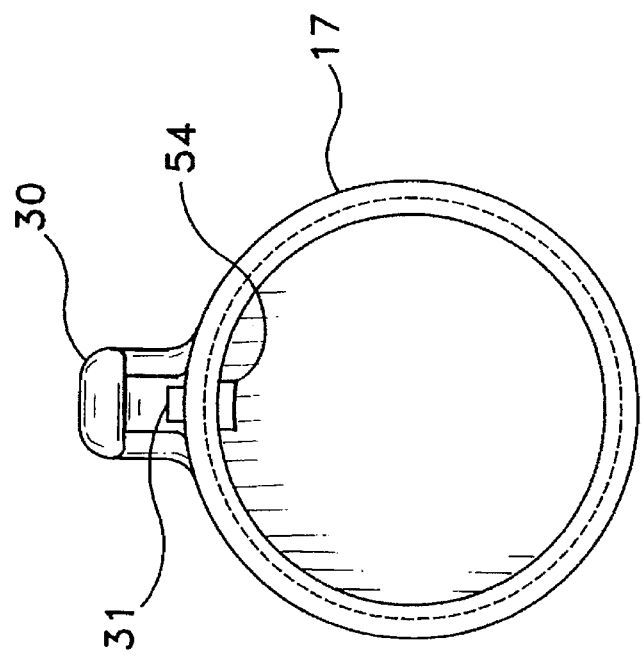

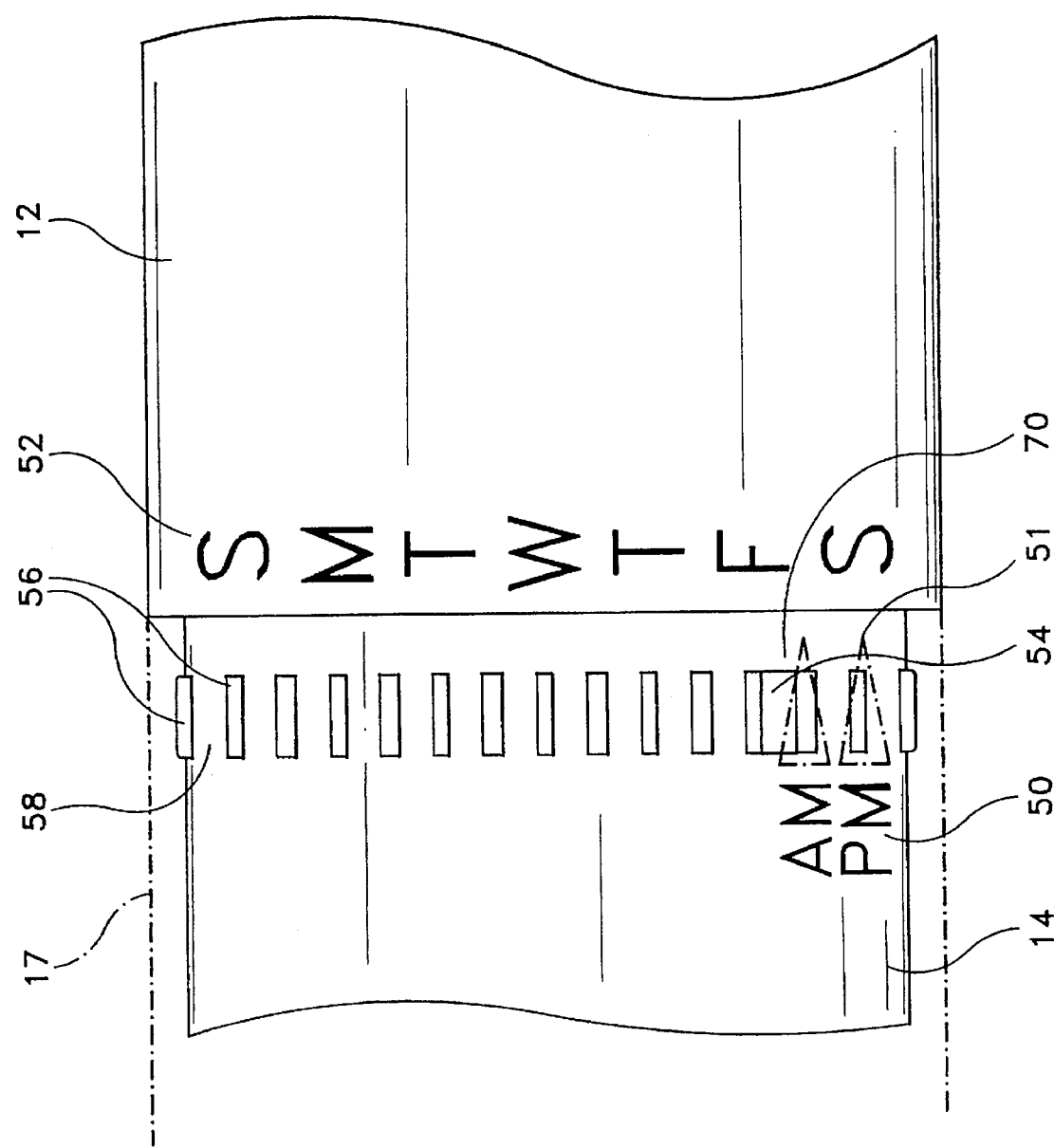

TIME OF LAST INJECTION INDICATOR FOR MEDICATION DELIVERY PEN

BACKGROUND OF THE INVENTION

1. Field of the Invention

The subject invention relates to an indicator for medication delivery pens that displays the time of last injection.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of a week or day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastometric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point cannula of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described reusable medication delivery pen is effective and much more convenient for self-administration of medication than the typical hypodermic syringe and separate medication vial. However, the disassembly of the pen to remove empty medication vials and to insert new ones is an inconvenience. As a result, disposable pens have been developed. The prior art disposable medication delivery pen includes a vial of insulin or other such medication permanently encapsulated therein. The patient need merely connect a double-ended needle cannula to the disposable pen for each administration of medication. The prior art disposable pen can be discarded when the supply of medication permanently encapsulated therein has been exhausted.

Disposable medication delivery pens offer certain conveniences to the patient who is required to self-administer medication. However, neither prior art disposable mediation delivery pens nor reusable medication delivery pens have addressed the problem of a user not remembering when the last injection was administered. Since the typical diabetes patient will require injections of insulin several times during the course of the week and may lose track of when the last injection was made, it is important to provide means for informing the user of the time of last injection.

SUMMARY OF THE INVENTION

The subject invention relates to a medication delivery pen having an indicator that displays the time of last injection through interaction between a cap and pen body assembly.

When a user requires an injection the cap is removed from a distal end of the pen body assembly of the medication delivery pen and a desired dose is set by the user turning a dose setting knob at a proximal end of the pen body assembly until the desired dose indicia is displayed in a window in the pen body assembly. After the desired dose is set using the dose setting knob, injection is achieved by the user pushing on an actuator button located at the proximal end of the pen body assembly. After injection, as the user replaces the cap on the distal end of the pen body assembly the cap is seated on the pen body assembly such that a time of day indicator on the cap is aligned with a day of the week indicator on the distal end of the pen body assembly to visually and/or tactilely display the day and time of day of the that injection.

The present invention, therefore, provides the user with very convenient means for remembering when the last injection was administered by aligning visual and/or tactile indicia on the cap with visual and/or tactile indicia on the pen body assembly, without having to otherwise write or record the day and time of the last injection.

DESCRIPTION OF THE DRAWINGS

FIG. 1 is a perspective view of the medication delivery pen of the subject invention.

FIG. 2 is an elevational view of the medication delivery pen shown in FIG. 1.

FIG. 4 is a proximal end elevational view of the cap shown in FIG. 3.

FIG. 5 is a proximal end elevational view of the pen body assembly on the medication delivery pen shown in FIG. 3.

FIG. 7 is a side view of the periphery of the medication delivery pen projected on a plane, showing the PM indicator of the cap pointing to the S indicator for Saturday on the medication delivery pen.

DETAILED DESCRIPTION

Figure 3:
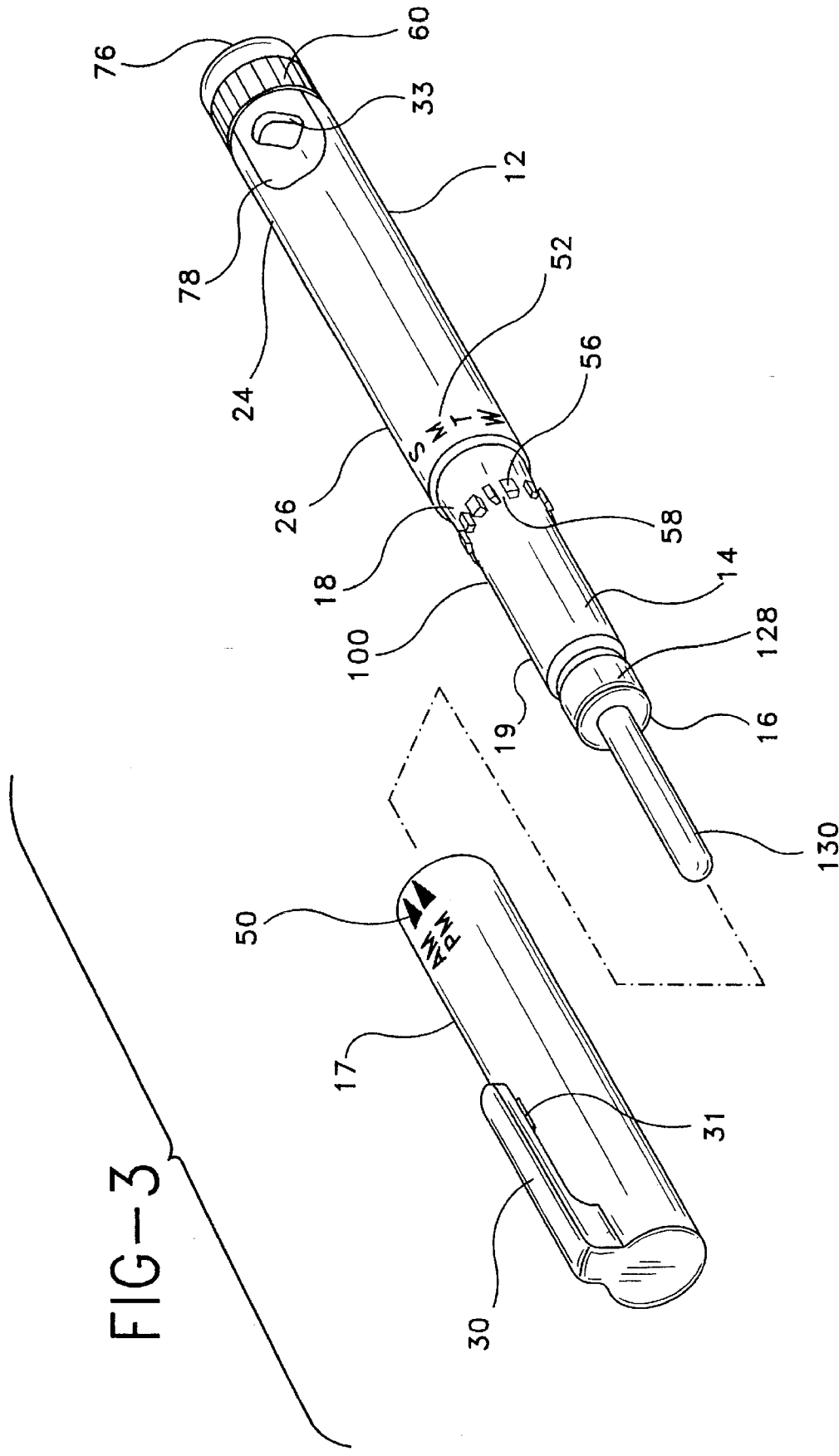
FIG. 3 is an exploded view of the medication delivery pen shown in FIGS. 1 and 2, with the cap removed.

A medication delivery pen in accordance with the subject invention is identified generally by numeral 10 in FIGS. 1 and 2. FIGS. 1 and 2 are a perspective view and an elevational view, respectively, of medication delivery pen 10 with a cap 17 attached to a distal end 26 of a pen body assembly 12. Medication delivery pen 10 includes a dose setting knob 60 rotatably attached to a proximal end 24 of pen body assembly 12 and an actuator button 76 rotatably attached to dose setting knob 60. Dose setting knob 60 is rotated by the user to set a desired dose for the next injection. As dose setting knob 60 is rotated it begins to telescope from proximal end 24 a predetermined distance for each dosage unit. When the desired dose has been set by the user, described further below, the user injects theirself with the dose by pushing actuator button 76 in the direction of a distal end 26 and thus pushing dose setting knob 60 back into pen body assembly 12.

Pen body assembly 12 includes an insert 78 in proximal end 24 having a window 33 through which a user reads dose setting indicia (not shown) on dose setting knob 60 when setting the desired dosage. Pen body assembly 12 also includes a set of visual and/or tactile indicia 52 around a circumference of distal end 26 that represent particular days of a week, e.g., M=Monday, T=Tuesday, etc.

Cap 17 includes a clip 30 attached to a distal end 32 with a protrusion 31 located on cap 17 underneath clip 30. Clip 30 is used to attach a capped medication delivery pen 10 to a flat surface during storage or transportation. A proximal end 34 of cap 17 attaches to distal end 26 of pen body assembly 12 and includes visual and/or tactile indicia 50 that represent different times of the day, e.g., AM and PM. When cap 17 is attached to distal end 26 of pen body assembly 12, one of the indicia 50 on cap 17 is aligned with one of the indicia 52 on pen body assembly 12 to permit the user to indicate and easily remember the time of the last injection.

FIG. 3 is an exploded view of medication delivery pen 10 with cap 17 removed from distal end 26. As shown in FIG. 3, medication delivery pen 10 also includes a cartridge holder assembly 14 with its proximal end 18 attached to distal end 26 of pen body assembly 12. Cartridge holder assembly 14 includes a medication cartridge (not shown) containing medication, e.g., insulin, sealed by a pierceable elastomeric seal (not shown). More particularly, the cartridge in cartridge holder assembly 14 will contain a volume of medication sufficient for administration of several doses. After exhaustion of the medication, cartridge holder assembly 14 can be threadedly disengaged from pen body assembly 12, discarded, and a new cartridge holder assembly 14 with a full medication cartridge may then be mounted to the reusable pen body assembly 12.

Medication delivery pen 10 also includes a needle cannula assembly 16 attached to a distal end 19 of cartridge holder assembly 14. Needle cannula assembly 16 includes a mounting hub 128 containing a double ended needle cannula (not shown) with a distal point cannula (not shown) extending in the distal direction and a proximal point cannula (not shown) extending into cartridge holder assembly 14 and piercing the seal on the medication cartridge within cartridge holder assembly 14. The relative location of mounting hub 128 ensures that the proximal point cannula of the needle cannula will pierce the seal, when mounting hub 128 is engaged with cartridge holder assembly 14. As shown in FIG. 3, the distal point cannula of needle cannula assembly 16 is covered by a needle shield 130 removably attached to mounting hub 128 to cover the distal point cannula of needle cannula assembly 16 and protect against accidental needle sticks until immediately prior to the next use of medication delivery pen 10.

Cartridge holder assembly 14, shown in FIG. 3, also includes a plurality of tabs 56 evenly located around the circumference of a housing 100 near proximal end 18, with a receiving port 58 located between each pair of tabs 56. FIGS. 4 and 5 are end elevational views of cap 17 and pen body assembly 12, respectively. FIG. 4 shows a key 54 extending into cap 17 directly under clip 30 that is received by one of the receiving ports 58 between a pair of tabs 56 on cartridge holder assembly 14, shown in FIG. 5, when cap 17 is attached to distal end 26 of pen body assembly 12 to prevent rotation of cap 17 on pen body assembly 12. As shown in FIG. 5, tabs 56 are positioned around the circumference of housing 100 of cartridge holder assembly 14 and are positioned so that when cap 17 is placed on distal end 26 of pen body assembly 12, key 54 is received by a specific one of the receiving ports 58, such that one of the indicia 50 is aligned with one of the indicia 52 on pen body assembly 12 to indicate the time of the last injection. When tab 54 is located in one of the receiving ports 58, cap 17 is prevented from rotating by the pair of tabs 56 on either side of receiving port 58. Since cap 17 is retained in location with respect with pen body assembly 12 the apparatus retains the time of last of injection that was set by the user until cap 17 is removed by the user to perform the next injection.

Figure 6:
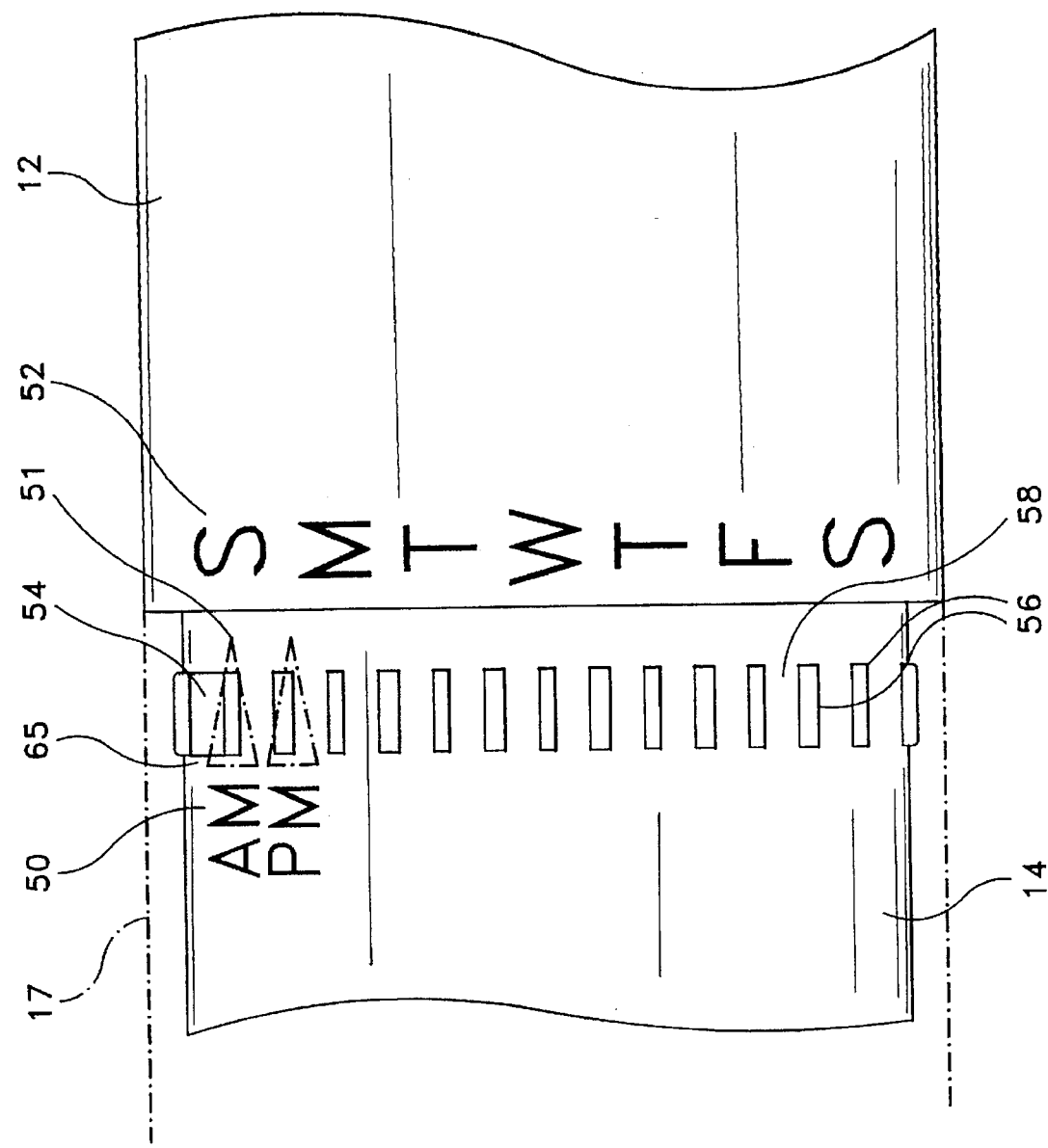
FIG. 6 is a side view of the periphery of the medication delivery pen projected on a plane, showing the AM indicator of the cap pointing to the S indicator for Sunday on the medication delivery pen.

For example, FIGS. 6 and 7 show key 54 located in two distinct receiving ports 58. In FIG. 6, the fixed position of cap 17 on pen body assembly 12 indicates that the time of last injection was Sunday, AM, since key 54 is located in receiving port 65. In FIG. 7, the fixed position of cap 17 on pen body assembly 12 causes key 54 to be located in receiving port 70 and thereby indicia 50 and 52 indicate that the time of last injection was Saturday, PM. As shown in FIGS. 6 and 7 there are fifteen tabs 56 and fourteen receiving ports 58 on housing 100, one receiving port 58 for AM and PM for each of the seven day in a week, i.e., S, M, T, W, R, F and S. Therefore, cap 17 and pen body assembly 12 can be oriented so to record fourteen different timed events. Of course, additional or fewer receiving ports could be used to provide more or less recordable events, if desired.

Medication delivery pen 10 may be stored with cap 17 attached thereto until a selected dose of medication is required. Just prior to use, cap 17 is removed and a new needle cannula assembly 16 is threadedly engaged to distal end 19 of cartridge holder assembly 14. The threaded engagement of needle cannula assembly 16 onto cartridge holder assembly 14 causes the proximal point cannula of needle cannula assembly 16 to pierce the seal of the medication holding cartridge within cartridge holder assembly 14 and provide communication with the medication contained therein. Shield 130 is then removed from needle cannula assembly 16 and a desired dose of medication is set by rotating dose setting knob 60 until indicia corresponding to the desired dose appears in window 33 of insert 78. The user then inserts the distal point cannula of needle cannula assembly 16 into their body and injects the dosage indicated by the indicia showing through window 33 by merely pushing actuator button 76 into proximal end 24 of pen body assembly 12.

After injection, cap 17 is mounted by the user over distal end 26 of pen body assembly 12, as described above, so that the time of last injection is indicated by the alignment of indicia 50 and 52. Medication delivery pen 10 is then stored or carried in a convenient location until the next dose of medication is required by the user. A subsequent dose of medication is then set in exactly the manner as described above. Dose setting and injections, of course, can be carded out until all of the medication in the medication cartridge in cartridge holder assembly 14 has been used. Cartridge holder assembly 14 may then be threadedly disengaged from pen body assembly 12, discarded and replaced.

While the invention has been described with respect to a preferred embodiment illustrated in FIGS. 1–7, it should be understood that variations from this preferred embodiment may be provided, and are considered to be within the scope of the subject invention.

What is claimed is:

1. A medication delivery pen comprising:

a pen body assembly comprising a distal end, a proximal end, means for setting a desired dose of medication to be dispensed by said pen body assembly and means for dispensing the desired dose of medication from the distal end of said pen body assembly, said pen body assembly including a plurality of indicia thereon;

a cap for covering said distal end of said pen body assembly, said cap having an indicia thereon; and means integral with and on said pen body assembly and said cap for indicating when the desired dose of medication was dispensed from said pen body assembly when said cap is attached to the distal end of said pen body assembly, wherein said indicating means is interposed between said distal end and said proximal end of said pen body assembly when said cap covers said distal end of said pen body assembly, wherein each of said plurality of indicia on said pen body assembly represent a day of a week, whereby said indicating means display the day of the week the desired dose was dispensed, when said cap is attached to the distal end of said pen body assembly, and wherein said indicia on said cap comprises an AM indicia and a PM indicia, whereby one of said cap indicia can be aligned with one of said plurality of indicia on said pen body assembly for said indicating means to display a time of day and the day of the week the desired dose was dispensed, when said cap is attached to the distal end of said pen body assembly.

2. The medication delivery pen of claim 1, wherein said means for indicating when the desired dose of medication was dispensed from said pen body assembly comprises a tactile display located on said cap and said pen body assembly.

3. The medication delivery pen of claim 1, wherein said means for indicating when the desired dose of medication was dispensed from said pen body assembly comprises a visual display located on said cap and said pen body assembly.

4. The medication delivery pen of claim 1, wherein said cap further comprises a protrusion extending into said cap and said pen body assembly further comprises a cartridge holder assembly at the distal end having a housing with a pair of tabs defining a receiving port for receiving said protrusion on said cap to prevent rotation of said cap on said pen body assembly when said cap is attached to the distal end of said pen body assembly.

5. The medication delivery pen of claim 1, wherein said means for dispensing the desired dose includes an actuator button rotatably mounted on the proximal end of said pen body assembly.

6. The medication delivery pen of claim 1, wherein said means for setting the desired dose of medication to be dispensed by said pen body assembly includes a dose setting knob rotatably mounted to the proximal end of said pen body assembly, wherein rotation of said dose setting knob causes said dose setting knob to telescope out of the proximal end of said pen body assembly.

7. A medication delivery pen comprising:

a pen body assembly comprising a distal end, a proximal end, means for setting a desired dose of medication to be dispensed by said pen body assembly, means for dispensing the desired dose of medication from said distal end of said pen body assembly, and a plurality of indicia representing particular days of a week;

a cap for covering said distal end of said pen body assembly having a plurality of indicia, each of said indicia representing a predetermined time of day; and means integral with and on said pen body assembly and said cap for indicating when the desired dose of medication was dispensed from said pen body assembly provided by aligning one of said time of day indicia on said cap with one of said plurality of day of the week indicia on said pen body assembly when said cap is attached to said distal end of said pen body assembly, wherein said indicating means is interposed between said distal end and said proximal end of said pen body assembly when said cap is attached to said distal end of said pen body assembly.

\* \* \* \* \*